(12) United States Patent
Beszant et al.

(10) Patent No.: US 8,742,080 B2
(45) Date of Patent: Jun. 3, 2014

(54) PROCESS FOR THE GLYCOSIDATION OF COLCHICINE AND THIOCOLCHICINE

(75) Inventors: Stephen Beszant, Milan (IT); Bruno Gabetta, Milan (IT)

(73) Assignee: Indena S.p.A., Milan (IT)

( * ) Notice: Subject to any disclaimer, the term of this patent is extended or adjusted under 35 U.S.C. 154(b) by 608 days.

(21) Appl. No.: 12/994,485

(22) PCT Filed: Apr. 9, 2009

(86) PCT No.: PCT/EP2009/002623
§ 371 (c)(1),
(2), (4) Date: Jan. 4, 2011

(87) PCT Pub. No.: WO2009/143930
PCT Pub. Date: Dec. 3, 2009

(65) Prior Publication Data
US 2011/0130554 A1 Jun. 2, 2011

(30) Foreign Application Priority Data

May 28, 2008 (EP) .................................... 08157069

(51) Int. Cl.
*C07H 15/248* (2006.01)
(52) U.S. Cl.
USPC ....................................................... 536/17.6
(58) Field of Classification Search
USPC ....................................................... 536/17.6
See application file for complete search history.

(56) References Cited

U.S. PATENT DOCUMENTS 5,777,136 A 7/1998 Bombardelli

FOREIGN PATENT DOCUMENTS

FR 2 112 131 6/1972

OTHER PUBLICATIONS

Gelmi et al, J. Med. Chem. 2007, 50, 2245-48.*
Osborn et al, Oligosaccharides: Their synthesis and biological roles, 2000, pp. 47-49.*
Greene et al, Protective Groups in Organic Synthesis, 2nd Ed., 1991, pp. 88-90.*

* cited by examiner

*Primary Examiner* — Ganapathy Krishnan
(74) *Attorney, Agent, or Firm* — Lucas & Mercanti, LLP

(57) ABSTRACT

A process for the preparation of compounds having formula (I) is disclosed, wherein: —$R_1$ is a methoxy or methylthio group; —$R_2$ is a O-glycosyloxy residue. Compounds having formula (I) are prepared by reacting the corresponding precursor having $R_2$=OH and the suitably protected 1-acetyl-glycose.

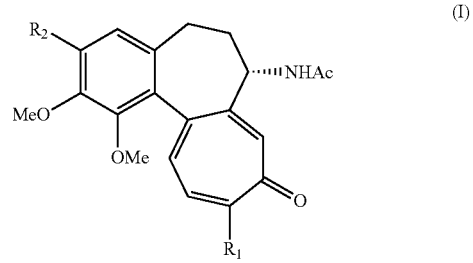

8 Claims, No Drawings

PROCESS FOR THE GLYCOSIDATION OF COLCHICINE AND THIOCOLCHICINE

This application is a U.S. national stage of PCT/EP2009/002623 filed on Apr. 9, 2009 which claims priority to and the benefit of European Application No. 08157069.9 filed on May 28, 2008, the contents of which are incorporated herein by reference.

TECHNICAL FIELD

The present invention discloses a process for the preparation of colchicine and thiocolchicine glycosides and derivatives thereof.

BACKGROUND OF THE INVENTION

Colchicine (I, $R_1=R_2=OMe$) is an alkaloid widely used for a long time in therapy for the treatment of gout. In addition, colchicine is a very potent antiblastic agent which acts by blocking the formation of the mitotic spindle in cell division; this property has been thoroughly investigated for any antitumoral activity, and a great number of colchicine derivatives have been prepared for this purpose. Colchicine and thiocolchicine (I, $R_1=SMe$, $R_2=OMe$) are the starting materials useful for the preparation of a series of active drugs.

3-O-Demethyl-thiocolchicine glucoside, or thiocolchicoside (I $R_1=SMe$, $R_2=\beta$-D-O-glucosyl), is an active ingredient of remarkably important use in the pharmaceutical field, mainly in the therapy of diseases of the muscle-skeletal system. 3-O-Demethylcolchicine glucoside, or colchicoside (I $R_1=OMe$, $R_2=\beta$-D-O-glucosyl), is also known and endowed with pharmacological activities.

Therefore, efficient methods for the glycosidation of colchicine-type compounds, to facilitate the preparation of both compounds and novel derivatives for use in pharmacological research, would be important.

FR 2112131 discloses a process for the glycosidation of thiocolchicine comprising the reaction of 2,3,4,6-tetra-O-acetyl-α-D-glucopyranosyl bromide with demethyl-thiocolchicine. This method is unsatisfactory due to the low yield and the time required for the lengthy and articulated process.

U.S. Pat. No. 5,777,136 describes a glycosidation process which involves the use of protected sugar fluorides, in particular protected derivatives of 1-fluoroglucose and 1-fluorofucose. The described process, in particular, is restricted to the preparation of 3-O-glucosyl or 3-O-fucosyl derivatives of colchicine and thiocolchicine. Even if the described yields are satisfactory, this method requires the preparation of suitably activated sugar derivatives, i.e. sugar fluorides, which means an additional step in the synthesis and the preparation and storage of reagents of relative stability.

SUMMARY OF THE INVENTION

The process of the invention is based on the use of protected 1-acetyl sugar derivatives and in particular peracetylated sugars in alternative to 1-halosugars, as glycosylating agents for colchicine or thiocolchicine substrates. These compounds are among the simplest, cheapest and definitely stable derivatives of monosaccharides, and their use is advantageous for the synthesis of glycosyl colchinoids.

The invention therefore relates to a process for preparing compounds having formula I:

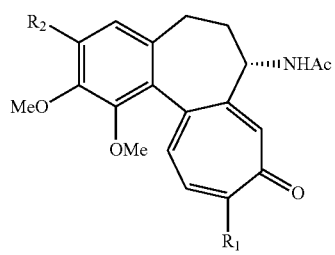

Formula I wherein:
$R_1$ is a methoxy or methylthio group;
$R_2$ is a O-glycosyloxy residue.

The process for the preparation of the compounds of formula I comprises the reaction of a protected 1-acetylated sugar with a compound having formula II:

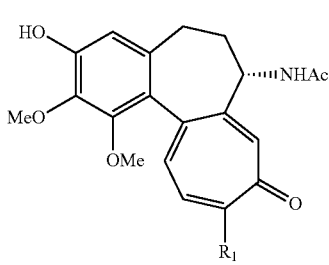

Formula II wherein $R_1$, is as defined above, followed by the cleavage of any protecting groups present in the glycosyl residue. 1-Acetyl-glycoses are usually protected by ester groups, typically acetyl groups, thus the final step of the process of the invention is the removal of the protective acetyl groups.

DETAILED DESCRIPTION OF THE INVENTION

The invention involves the reaction of a protected 1-acetyl-sugar with a compound having formula II. The obtained product is then submitted to cleavage of the protective groups present on the glycose residue to form a colchicine or thiocolchicine glycoside having formula I wherein:
$R_1$ is a methoxy or methylthio group;
$R_2$ is a O-glycosyloxy residue.

The glycosidation reaction is preferably carried out in a solvent selected from acetonitrile, nitromethane, halogenated hydrocarbons and mixtures thereof. The use of acetonitrile is particularly preferred. The reaction is carried out in the presence of a Lewis acid, preferably boron trifluoride, for a time ranging from 15 minutes to 6 hours, preferably from 30 minutes to 2 hours, at temperatures from 0° C. to the solvent's reflux temperature, preferably at room temperature, under inert atmosphere. The presence of an organic base is also required for the reaction to proceed. The use of 1,1,3,3-tetramethylguanidine is particularly preferred. The process of the invention has the advantage of being stereoselective providing just one of the two possible anomeric isomers. In particular, in the case of the sugars belonging to the gluco-series (equatorial C-2 substituent, as in D-glucose, D-galactose and D-xylose) the β-(1,2-trans) isomer is obtained selectively. With sugars belonging to the manno-series (axial C-2 substituent, as in L-rhamnose) as starting material, the α-(1, 2-trans) isomer is formed exclusively. The removal of the protective groups can be performed by basic hydrolysis in aqueous media, especially when the intermediate peracetyl glycoside is not isolated, or by nucleophilic displacement, e.g. with secondary amines such as dimethylamine, diethylamine, pirrolidine, piperidine or similar.

An improved process for the synthesis of the well-known thiocolchicoside or 3-O-β-D-glucopyranosyl-3-O-demethylthiocolchicine is also a specific object of the present invention.

The process of the invention provides a variety of advantages over known methods for the preparation of colchicine and thiocolchicine or derivatives thereof. These advantages include:
- the bypass of the preparation of a suitably activated glycosyl reactant, such as the 1-halo-sugar;
- the use of stable and easily prepared 1-acetyl-protected-glycoses (e.g. peracetylglycoses);
- the possibility of crystallizing the final product directly from the crude reaction mixture;
- the preparation of glycosyl colchinoids hardly obtainable with prior art methods, such as galactosides, rhamnosides, etc.

EXAMPLES

The following examples illustrate the invention in further detail.

1) Synthesis of thiocolchicoside (3-O-β-D-glucopyranosyl-3-O-demethylthiocolchicine)

3-O-demethylthiocolchicine (2.0 g) is suspended in acetonitrile (20 ml) under nitrogen atmosphere at room temperature, followed by sequential addition of 1,1,3,3-tetramethylguanidine (1.8 ml), a solution of 1,2,3,4,6-penta-O)-acetyl-β-D-glucopyranose (5.60 g) in acetonitrile (10 ml) and eventually boron trifluoride (7.2 ml).

The reaction mixture is stirred at room temperature for 2 hours, then cooled to 5° C. and quenched by addition of 2M KOH to pH≈6 (about 20 ml). The aqueous layer is separated and extracted with acetonitrile (10 ml). The combined organic layers are sequentially washed with $NaHSO_4$ 0.5 M (20 ml), $NaHCO_3$ 6% (20 ml) and brine (20 ml).

The solvent is removed under vacuum and replaced with 95% ethanol (30 ml). 2 M NaOH (40 ml) is added and the solution stirred until completion (about 2 hours).

1 M $NaHSO_4$ is added to pH=7, then ethanol is evaporated off under vacuum.

The aqueous layer is extracted twice with dichloromethane (2×20 ml) and the organic phase back-extracted with water (20 ml), then discarded. The combined aqueous layers are extracted with a dichloromethane-ethanol 1:1 mixture until complete extraction of thiocolchicoside. The organic layer is washed with 20% NaCl solution (30 ml), then concentrated to 20 ml and left to crystallize under stirring for 2 h at room temperature. The product is collected by filtration. 2.00 g of thiocolchicoside are obtained (71% yield) with physical and spectroscopic data identical to the those reported in literature.

2) Synthesis of 3-O-β-D-galactopyranosyl-3-O-demethylthiocolchicine

3-O-demethylthiocolchicine (1.0 g) is suspended in acetonitrile (10 ml) under nitrogen atmosphere at room temperature, followed by sequential addition of 1,1,3,3-tetramethylguanidine (0.9 ml), a solution of 1,2,3,4,6-penta-O-acetyl-β-D-galactopyranose (2.80 g) in acetonitrile (10 ml) and eventually boron trifluoride (3.6 ml).

The reaction mixture is stirred at room temperature for 2 hours, then cooled to 5° C. and quenched by addition of 2 M NaOH to pH≈6 (about 10 ml). The aqueous layer is separated and extracted with acetonitrile (10 ml). The combined organic layers are sequentially washed with 1 M $NaHSO_4$ (10 ml), 6% $NaHCO_3$ (10 ml) and brine (10 ml).

The solvent is removed under vacuum and replaced with 95% ethanol (20 ml). 2 M NaOH (20 ml) is added and the solution stirred until completion (about 2 hours).

0.5 M $NaHSO_4$ is added to pH=7, then ethanol is evaporated off under vacuum.

The aqueous layer is extracted twice with dichloromethane (2×20 ml) and the organic phase back-extracted with water (20 ml), then discarded. The combined aqueous layers are extracted with a dichloromethane-ethanol 1:1 mixture until complete extraction of thiocolchicoside. The organic layer is washed with 20% NaCl solution (20 ml), then the solvent is replaced with methanol and concentrated to 15 ml and left to crystallize under stirring for 2 h at room temperature. The product is collected by filtration. 855 mg of product are obtained (61% yield), mp=255-6° C.

$^1$H-NMR (DMSO-$d_6$) δ (ppm): 1.86 (1H, m); 1.87 (3H, s); 2.06 (1H, m); 2.24 (1H, m); 2.43 (3H, s); 2.55 (1H, m); 3.45 (1H, m); 3.57 3H, s); 3.60 (1H, m); 3.62 (1H, m); 3.67 (1H, m); 3.74 (1H, m); 3.87 (3H, s); 4.36 (1H, m); 4.52 (1H, d, J=4.4 Hz); 4.68 (1H, t, J=5.7 Hz); 4.85 (1H, d, J=5.7 Hz); 4.91 (1H, d, J=7.8 Hz); 5.14 (1H, d, J=5.6 Hz); 6.88 (1H, s); 7.04 (1H, s); 7.17 (1H, d, J=10.7 Hz); 7.29 (1H, d, J=10.7 Hz); 8.60 (1H, d, J=7.3 Hz).

MS$^+$ (m/z): 1149.0 [2 M+Na]$^+$, 1126.7 [2 M+H]+, 586.3 [M+Na]+, 564.2 [M+H]$^+$, 402.2 [M-gal+H]$^+$.

3) Synthesis of 3-O-α-L-rhamnopyranosyl-3-O-demethylthiocolchicine

3-O-demethylthiocolchicine (2.0 g) is suspended in acetonitrile (20 ml) under nitrogen atmosphere at room temperature, followed by sequential addition of 1,1,3,3-tetramethylguanidine (1.8 ml), a solution of 1,2,3,4-tetra-O-acetyl-β-L-rhamnopyranose (4.77 g) in acetonitrile (10 ml) and eventually boron trifluoride (8.4 ml).

The reaction mixture is stirred at room temperature for 3 hours, then cooled to 5° C. and quenched by addition of 2 M NaOH to pH≈6. The aqueous layer is separated and extracted with acetonitrile. The combined organic layers are sequentially washed with 1 M $NaHSO_4$, 6% $NaHCO_3$ and brine.

The solvent is removed under vacuum and replaced with 95% ethanol (20 ml). 2 M NaOH (15 ml) is added and the solution stirred until completion (about 2 hours).

1 M $NaHSO_4$ is added to pH=7, then ethanol is evaporated under vacuum.

The aqueous layer is extracted twice with dichloromethane (2×20 ml) and the organic phase back-extracted with water (20 ml), then discarded. The combined aqueous layers are extracted with a dichloromethane-ethanol 1:1 mixture until complete extraction of thiocolchicoside. The organic layer is washed with 20% NaCl solution (30 ml then the solvent is replaced with methanol and concentrated to 15 ml and left to crystallize under stirring for 2 h at room temperature. The product is collected by filtration. 2.03 g of 3-O-α-L-rhamnopyranosyl-3-O-demethylthiocolchicine are obtained (78% yield), mp=254-5° C.

$^1$H-NMR (DMSO-$d_6$) δ (ppm): 1.19 (3H, d, J=6.6 Hz); 1.87 (1H, m); 1.88 (3H, s); 2.04 (1H, m); 2.22 (1H, m); 2.44 (3H, s); 2.61 (1H, m); 3.35 (1H, m); 3.59 (3H, s); 3.70 (1H, m); 3.71 (1H, m); 3.85 (3H, s); 4.35 (1H, m); 4.82 (1H, d, J=5.7 Hz); 4.94 (1H, d, J=5.7 Hz); 5.12 (1H, d, J=4.3 Hz);

5.39 (1H, d, J=1.8 Hz); 6.88 (1H, s); 7.05 (1H, s); 7.16 (1H, d, J=10.7 Hz); 7.29 (1H, d, J=10.7 Hz); 8.68 (1H, d, J=7.5 Hz).

MS$^+$ (m/z): 1117.1 [2 M+Na]$^+$, 570.3 [M+Na]$^+$, 548.2 [M+H]$^+$, 402.2 [M-rha+H]$^+$.

4) Synthesis of 3-O-β-D-xylopyranosyl-3-O-demethylthiocolchicine 15.0 g of 3-O-demethylthiocolchicine are suspended in 140 ml of acetonitrile under stirring in a nitrogen atmosphere.

13.5 ml of 1,1,3,3-tetramethylguanidine are added turning the mixture into a blood red solution. A solution of 34.3 g of D-xylose tetraacetate in 60 ml of acetonitrile are added and eventually 45 ml of BF$_3$.Et$_2$O are added dropwise keeping the internal temperature at around 20° C. The solution is stirred for 2 h until completion, then cooled to 5° C. and adjusted to pH~7 with 120 ml of 2 M NaOH.

The phases are separated and the aqueous phase back-extracted with 25 ml of acetonitrile. The organic layer is washed sequentially with 50 ml of 1 M NaHSO$_4$, 60 ml of 5% NaHCO$_3$ and eventually with 50 ml of brine. The organic layer is concentrated to a volume of 150 ml, 50 ml of tert-butylmethyl ether are added and the mixture left to crystallize at room temperature for 1 h. The solid is collected by filtration, washed with 40 ml of acetonitrile-tert-butylmethyl ether 1:1 and dried to yield 19.8 g of 3-O-β-D-(2',3',4'-triacetyl) xylopyranosyl-3-O-demethylthiocolchicine.

19.4 g of this intermediate are suspended in 300 ml of methanol, 16 ml of diethylamine are added and the mixture heated to 40° C. for 2 h until completion.

The resulting solution is concentrated to a volume of 110 ml and allowed to crystallize for 1 h at room temperature. The solid is collected by filtration, washed with 25 ml of methanol and dried to yield 13.7 g of product (overall yield: 70%), mp=233-4° C.

IR cm$^{-1}$: 3295, 2940, 2867, 1636, 1601, 1558, 1507, 1480, 1424, 1348, 1317, 1074, 1029, 870, 594.

$^1$H-NMR (DMSO-d$_6$) δ (ppm): 1.86 (1H, m); 1.87 (3H, s); 2.04 (1H, m); 2.24 (1H, m); 2.43 (3H, s); 2.61 (1H, m); 3.28 (1H, m); 3.31 (1H, m); 3.33 (1H, m); 3.43 (1H, m); 3.57 (3H, s); 3.82 (1H, dd, J=11.2 Hz, 5.1 Hz); 3.86 (3H, s); 4.36 (1H, m); 4.98 (1H, d, J=7.2 Hz); 5.08 (1H, d, J=4.8 Hz); 5.11 (1H, d, J=4.8 Hz); 5.34 (1H, d, J=5.7 Hz); 6.86 (1H, s); 7.05 (1H, s); 7.16 (1H, d, J=10.7 Hz); 7.28 (1H, d, J=10.7 Hz); 8.60 (1H, d, J=7.3 Hz).

MS$^+$ (m/z): 1067.7 [2 M+Na]$^+$, 1066.5 [2 M+H]$^+$, 556.2 [M+Na]$^+$, 534.2 [M+H]$^+$, 402.2 [M-xyl+H]$^+$.

5) Synthesis of 3-O-β-D-xylopyranosyl-3-O-demethylcolchicine 2.0 g of 3-O-demethylcolchicine are suspended in 18 ml of acetonitrile under stirring in a nitrogen atmosphere.

1.9 ml of 1,1,3,3-tetramethylguanidine are added turning the mixture into a blood red solution. A solution of 4.9 g of D-xylose tetraacetate in 10 ml of acetonitrile is added and eventually 5.2 ml of BF$_3$.Et$_2$O are added dropwise keeping the internal temperature at around 20° C. The solution is stirred for 2 h until completion, then cooled to 5° C. and adjusted to pH~7 with 2 M NaOH.

The phases are separated and the aqueous phase back-extracted with 10 ml of acetonitrile. The organic layer is washed sequentially with 1 M NaHSO$_4$, 5% NaHCO$_3$ and eventually with brine. The solvent is replaced with methanol (30 ml), 6.4 ml of diethylamine are added and the mixture heated to 40° C. for 2 h until completion.

The solvent is evaporated and the residue purified by column chromatography with DCM:MeOH 85:15. Fractions containing the product are collected and the solvent removed to yield 2.29 g of an amorphous product (overall yield: 86%).

$^1$H-NMR (DMSO-d$_6$) δ (ppm): 1.86 (1H, m); 1.87 (3H, s); 2.03 (1H, m); 2.23 (1H, m); 2.59 (1H, m); 3.28 (1H, m); 3.31 (1H, m); 3.33 (1H, m); 3.42 (1H, m); 3.55 (3H, s); 3.81 (1H, dd, J=10.8 Hz, 5.0 Hz); 3.86 (3H, s); 3.90 (3H, s); 4.35 (1H, m); 4.97 (1H, d, J=7.2 Hz); 5.06 (1H, d, J=4.6 Hz); 5.10 (1H, d, J=4.8 Hz); 5.33 (1H, d, J=5.3 Hz); 6.84 (1H, s); 7.04 (1H, d, J=10.7 Hz); 7.12 (1H, d, J=10.7 Hz); 7.15 (1H, s); 8.60 (1H, d, J=7.3 Hz). MS$^+$ (m/z): 1056.8 [2M+Na]$^+$, 540.3 [M+Na]$^+$, 518.2 [M+H]$^+$, 386.2 [M-xyl+H]$^+$.

The invention claimed is:
1. A process to prepare compounds having formula I:

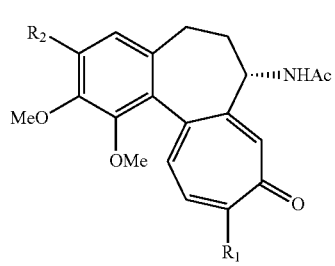

Formula I wherein:
R$_1$ is a methoxy or a methylthio group;
R$_2$ is a O-glycosyloxy residue;
said process comprising reacting a protected 1-acetyl-glycose with a compound having formula II:

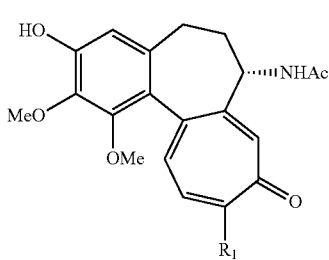

Formula II wherein R$_1$ is as defined above in the presence of a Lewis acid and an organic base, removing the protecting groups from the glycosyl moiety; and obtaining compounds having formula I.

2. The process of claim 1 where said 1-acetyl-glycose, of either the D or L-series, are protected by ester groups.

3. A process according to claim 2 wherein the ester groups are acetyl groups.

4. The process of claim 1 wherein said protecting groups are cleaved by basic hydrolysis.

5. The process of claim 1 wherein said protecting groups are cleaved through nucleophilic displacement by reaction with an amine.

6. The process of claim 1 wherein the reacting step is carried out in a solvent selected from the group consisting of acetonitrile, nitromethane, halogenated hydrocarbons and mixtures thereof.

7. The process of claim 1 wherein the Lewis acid is boron trifluoride.

8. The process of claim 1 wherein said base is 1,1,3,3-tetramethylguanidine.

\* \* \* \* \*